US012577619B1

(12) United States Patent
Ali

(10) Patent No.: US 12,577,619 B1
(45) Date of Patent: Mar. 17, 2026

(54) BIOMARKER FOR DETECTING AND TREATING TYPE II DIABETES

(71) Applicant: KUWAIT UNIVERSITY, Safat (KW)

(72) Inventor: Hamad Ali, Safat (KW)

(73) Assignee: KUWAIT UNIVERSITY, Safat (KW)

( * ) Notice: Subject to any disclaimer, the term of this patent is extended or adjusted under 35 U.S.C. 154(b) by 0 days.

(21) Appl. No.: 19/297,604

(22) Filed: Aug. 12, 2025

(51) Int. Cl.
*C12Q 1/68* (2018.01)
*C12Q 1/6883* (2018.01)

(52) U.S. Cl.
CPC ..... *C12Q 1/6883* (2013.01); *C12Q 2600/158* (2013.01)

(58) Field of Classification Search
CPC ................................................... C12Q 1/6883
See application file for complete search history.

(56) References Cited

U.S. PATENT DOCUMENTS

2014/0309280 A1 * 10/2014 Hudson ................ C12N 15/113
536/24.31

FOREIGN PATENT DOCUMENTS

| CN | 115896274 A | 4/2023 | |
|----|-------------|--------|---|
| CN | 116179687 A | 5/2023 | |
| WO | 2023004079 A2 | 1/2023 | |
| WO | WO-2023177132 A1 * | 9/2023 | ........... C12Q 1/6883 |

OTHER PUBLICATIONS

Zeng et al., Clin. Chim. Acta 518, 33-37 (2021). (Year: 2021).*
Wang et al., J. Cell Mol. Med. 25, 4893-4901 (2021). (Year: 2021).*
Li, et al.; "Serum-derived piR-hsa-164586 of extracellular vesicles as a novel biomarker for early diagnosis of non-small cell lung cancer"; Front. Oncol., Sep. 27, 2022 Sec. Thoracic Oncology vol. 12—2022 | https://doi.org/10.3389/fonc.2022.850363.
Henaoui, et al.; "PIWI-interacting RNAs as novel regulators of pancreatic beta cell function"; Received: Jan. 20, 2017 /Accepted: Jun. 1, 2017 /Published online: Jul. 16, 2017.

* cited by examiner

*Primary Examiner* — Kenneth R Horlick
(74) *Attorney, Agent, or Firm* — Nath, Goldberg & Meyer; Joshua B. Goldberg

(57) ABSTRACT

A method for detecting and treating Type II Diabetes includes the use of hsa_piR_020485, a PIWI-interacting RNA isolated from urinary extracellular vesicles (ECVs), as a biomarker for the diagnosis and treatment of Type 2 diabetes mellitus (T2DM). The method is non-invasive, utilizing the differential expression of hsa_piR_020485 in diabetic versus non-diabetic subjects to identify subjects in need of treatment for T2DM. The method includes obtaining a urine sample from a subject, isolating urinary ECVs from the urine sample, extracting total RNA from the isolated urinary ECVs, quantifying hsa_piR_020485 levels from the total RNA, determining if the hsa_piR_020485 expression level exceeds a threshold, and administering one or more T2DM treatments.

2 Claims, 3 Drawing Sheets

Specification includes a Sequence Listing.

A

B

C

BIOMARKER FOR DETECTING AND TREATING TYPE II DIABETES

SEQUENCE LISTING

The instant application contains a Sequence Listing which has been submitted in XML format via EFS-Web and is hereby incorporated by reference in its entirety. Said XML copy, created on Jun. 9, 2025, is named 33044.81U Sequence Listing and is 1,684 bytes in size.

FIELD AND BACKGROUND OF THE INVENTION

The disclosure of the present patent application relates to a biomarker for detecting and treating Type II Diabetes and particularly to a method of detecting hsa_piR_020485, a PIWI-interacting RNA, in human urine as a critical step in a noninvasive diagnostic method for detecting and treating Type II Diabetes mellitus.

DESCRIPTION OF THE PRIOR ART

Type 2 diabetes mellitus (T2DM) is a serious chronic disease that remains a major global health concern, recognized as a significant determinant of mortality and decreased life expectancy worldwide. Its prevalence, along with its associated complications, continues to rise without any indication of slowing. The disease is anticipated to have a severe impact on public health and place a substantial economic burden on global healthcare systems in the coming years. (Lin X., et al., "Global, regional, and national burden and trend of diabetes in 195 countries and territories: an analysis from 1990 to 2025", Sci Rep 2020; 10 (1): 14790.) IDF projections indicate that the global number of adults with T2DM is expected to reach almost 700 million by 2045 if effective prevention strategies are not implemented. (Lin et al.) Thus, there is an ongoing need for sensitive and reliable biomarkers that can help address diagnostic gaps by enabling early detection, disease stratification, and risk prediction. This is crucial for implementing more effective therapeutic interventions and subsequently reducing the risk of disease progression.

Piwi-interacting RNAs (piRNAs), a class of small non-coding RNAs typically 24-31 nucleotides long, were initially recognized for their role in silencing transposable elements and preserving genomic integrity in germ cells. (Ozata D. M., et al., "PIWI-interacting RNAs: small RNAs with big functions", Nat Rev Genet 2019; 20 (2): 89-108.) However, they are now emerging as potential regulators in metabolic disorders like T2DM. (Henaoui I. S., et al., "PIWI-interacting RNAs as novel regulators of pancreatic beta cell function", Diabetologia 2017; 60 (10): 1977-1986.) Studies have revealed altered piRNA expression profiles in individuals with T2DM, implicating them in processes such as pancreatic β-cell dysfunction, insulin resistance, and chronic inflammation. (Zeng Q., et al., "PIWI-interacting RNAs and PIWI proteins in diabetes and cardiovascular disease: Molecular pathogenesis and role as biomarkers", Clin Chim Acta 2021; 518:33-37; Wang T., et al., "Emerging functions of piwi-interacting RNAs in diseases", J Cell Mol Med 2021; 25 (11): 4893-4901.)

Thus, a Biomarker for Detecting and Treating Type II Diabetes solving the aforementioned problems is desired.

SUMMARY OF THE INVENTION

The biomarker for detecting and treating Type II Diabetes includes the use of hsa_piR_020485, a PIWI-interacting RNA isolated from urinary extracellular vesicles (ECVs), as a biomarker for the diagnosis and treatment of Type 2 diabetes mellitus (T2DM). These methods include non-invasive, diagnostic methods, utilizing the differential expression of hsa_piR_020485 in diabetic versus non-diabetic subjects to identify subjects in need of treatment for T2DM. The methods disclosed herein include obtaining a urine sample from a subject, isolating urinary ECVs from the urine sample, extracting total RNA from the isolated urinary ECVs, and quantifying hsa_piR_020485 levels from the total RNA using next-generation sequencing technology. A significant upregulation of hsa_piR_020485 expression is observed in subjects suffering from T2DM, which may then be administered one or more T2DM treatments.

In an embodiment, a receiver operating characteristic (ROC) analysis demonstrates that the use of hsa_piR_020485 as a diagnostic biomarker of T2DM provides high diagnostic accuracy (AUC=0.94). The methods disclosed herein offer a highly specific and sensitive tool for early T2DM detection, providing a practical and efficient alternative to traditional diagnostic approaches. The biomarker for detecting and treating T2DM has potential clinical applications in routine diabetes screening and disease monitoring, aiding in early intervention and improved patient outcomes.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1A:
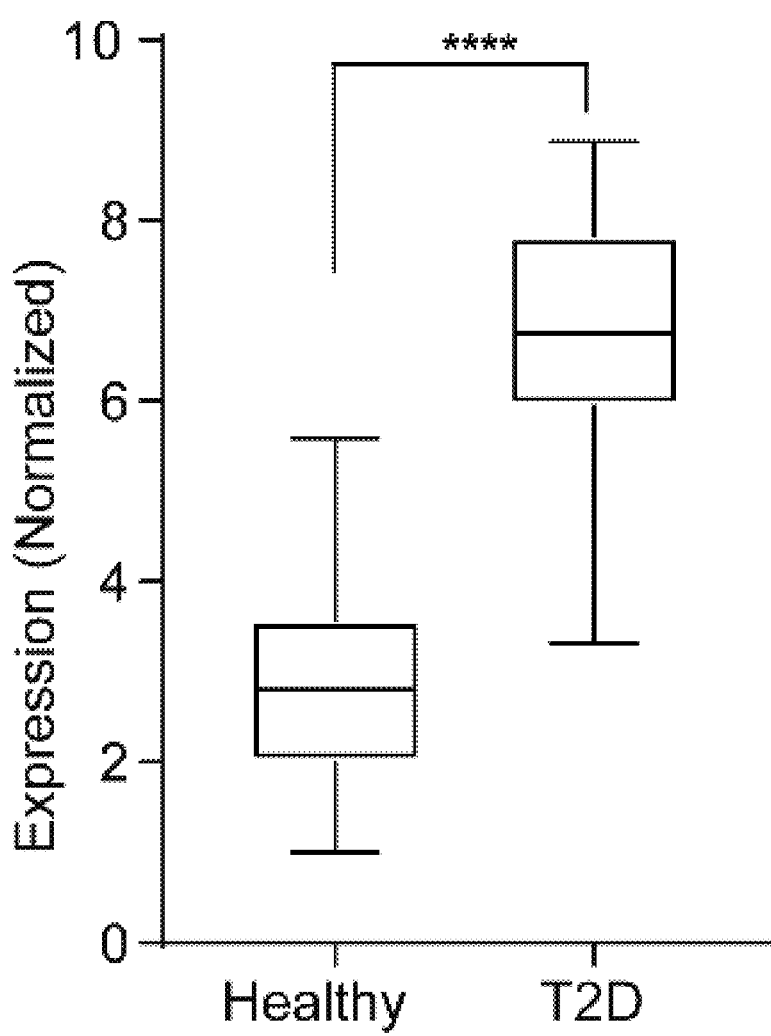
FIG. 1A is a box plot illustrating the normalized expression levels of hsa_piR_020485 in healthy individuals and T2DM patients, showing a significant upregulation in the T2D group ($p<0.0001$).

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as Type II Diabetes Mellitus.

As used herein, hsa_piR_020485 refers to a non-coding RNA comprising the 30 nucleotide sequence: GGCGG-GAGTAACTATGACTCTCTTAAGGTA (SEQ ID NO: 1). This sequence has also been referred to in the scientific literature as DQ597997.1, hsa_piRNA_26008, hsa_piR_020381, piR-36063, piR-hsa-28212, and URS0000033B5D.

The biomarker for detecting and treating Type II Diabetes includes the use of hsa_piR_020485, a PIWI-interacting RNA isolated from urinary extracellular vesicles (ECVs), as a biomarker for the diagnosis and treatment of Type 2 diabetes mellitus (T2DM). These methods include non-invasive, diagnostic methods, utilizing the differential expression of hsa_piR_020485 in diabetic versus non-diabetic subjects to identify subjects in need of treatment for T2DM. The methods disclosed herein include obtaining a urine sample from a subject, isolating urinary ECVs from the urine sample, extracting total RNA from the isolated urinary ECVs, and quantifying hsa_piR_020485 levels from the total RNA using next-generation sequencing technology. A significant upregulation of hsa_piR_020485 expression is observed in subjects suffering from T2DM, which may then be administered one or more T2DM treatments.

In an embodiment, the method is non-invasive, utilizing the differential expression of hsa_piR_020485 in diabetic versus non-diabetic subjects to identify subjects in need of treatment for T2DM.

In an embodiment, the method includes obtaining a urine sample from a subject, isolating urinary ECVs from the urine sample, extracting total RNA from the isolated urinary ECVs, quantifying hsa_piR_020485 levels from the total RNA, determining if the hsa_piR_020485 expression level exceeds a threshold, and administering one or more T2DM treatments. The optimal diagnostic cut-off threshold for hsa_piR_020485 may be 2.13 normalized log 2 expression units. The diagnostic cut-off threshold may provide 87.5% sensitivity and 92.9% specificity. The diagnostic cut-off threshold may have a significant positive correlation with HbA1c levels ($R=0.26$, $p=0.036$) (See FIG. 1C).

In an embodiment, a receiver operating characteristic (ROC) analysis demonstrates that the use of hsa_piR_020485 as a diagnostic biomarker of T2DM provides high diagnostic accuracy ($AUC=0.94$). The methods disclosed herein offer a highly specific and sensitive tool for early T2DM detection, providing a practical and efficient alternative to traditional diagnostic approaches. The biomarker for detecting and treating T2DM has potential clinical applications in routine diabetes screening and disease monitoring, aiding in early intervention and improved patient outcomes.

A subject suffering from T2DM may be treated by adhering to an increased exercise regimen, adhering to a diet reducing overall caloric intake, or administering a pharmaceutical treatment for T2DM.

Pharmaceutical treatments for T2DM may include any pharmaceutical now known or later developed, including but not limited to administering one or more pharmaceuticals selected from the group consisting of metformin, a sulfonylurea, a glinide, a thiazolidinedione, a DPP-4 inhibitor, a GLP-1 receptor agonist, and a SGLT2 inhibitor.

The present methods may be better understood in view of the following Examples

EXAMPLE 1

Sample Collection, ECV Isolation, and piRNA Quantification

Urine samples were collected using standard clinical procedures and urinary ECVs were isolated from the urine samples using ultracentrifugation. Successful isolation of urinary ECVs was confirmed using electron microscopy and flow cytometry analysis of markers CD63, TSC-101, and GRP94.

RNA libraries were prepared using a QIAseq miRNA Library Kit (331502, Qiagen, Hilden, Germany), in accordance with manufacturer's instructions. RNA was extracted from the urinary ECVs using a Urine Exosome Purification and RNA Isolation Maxi Kit (58800, Norgen Biotech Corp.), in accordance with manufacturer's instructions. Sequencing was carried out using a MiSeq 150 cycle version 3 kit (MS-102-3001, Illumina Inc., San Diego, CA, USA) in accordance with manufacturer's instructions. Quantification of mature piRNA annotations was performed by counting the read alignment reported by the BQA output.

A cut-off threshold for hsa_piR_020485 expression was determined to T2DM diagnosis, including consideration of correlations between hsa_piR_020485 expression and HbA1C, fasting glucose, and insulin levels. The optimal diagnostic cut-off threshold for hsa_piR_020485 expression was determined using the Youden Index method from ROC analysis, yielding a threshold of 2.13 normalized log 2 expression units, which provided 87.5% sensitivity and 92.9% specificity. Further, correlation analysis using Pearson's method revealed a significant positive correlation with HbA1c levels (R=0.26, p=0.036) (See FIG. 1C). These findings suggest that hsa_piR_020485 may serve as a non-invasive biomarker for T2DM diagnosis and glycemic monitoring.

EXAMPLE 2

Comparing Hsa_piR_020485 Expression in T2DM and Healthy Individuals

Peripheral blood samples (10 mL) were collected in EDTA-coated tubes and centrifuged at 1,600×g for 10 minutes to separate the plasma, which was then aliquoted and stored at −80° C. until further processing. Extracellular vesicles (EVs) were isolated from plasma using a combination of ultracentrifugation and size filtration. Total RNA, including small RNA species, was subsequently extracted using the Norgen Urine Exosome RNA Isolation Maxi Kit (Cat. No. 58800). RNA yield was quantified using a Qubit fluorometer, and quality was assessed using the Agilent Bioanalyzer. For sequencing, libraries were prepared with the Qiagen QIAseq miRNA Library Kit, following the manufacturer's instructions for adapter ligation, UMI tagging, cDNA synthesis, and PCR amplification. Sequencing was carried out on the Illumina MiSeq platform using the 150-cycle v3 kit. Raw reads (FASTQ files) were processed and analyzed using Qiagen's GeneGlobe data analysis pipeline, and miRNA expression levels were normalized using the Trimmed Mean of M-values (TMM) method.

Figure 1B:
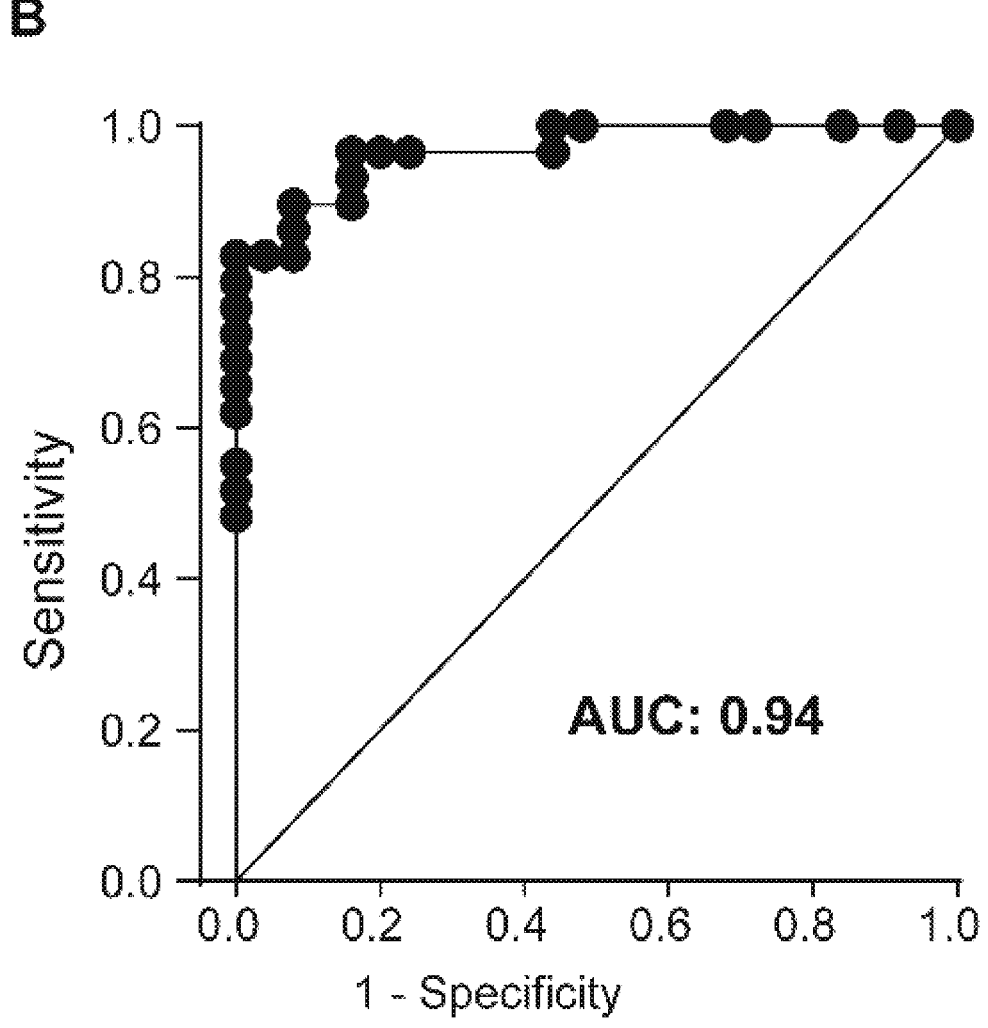
FIG. 1B depicts a receiver operating characteristic (ROC) curve, assessing the diagnostic performance of hsa_piR_020485 in distinguishing T2DM patients from healthy controls, with an area under the curve (AUC) of 0.94, indicating strong discriminative power.
Figure 1C:
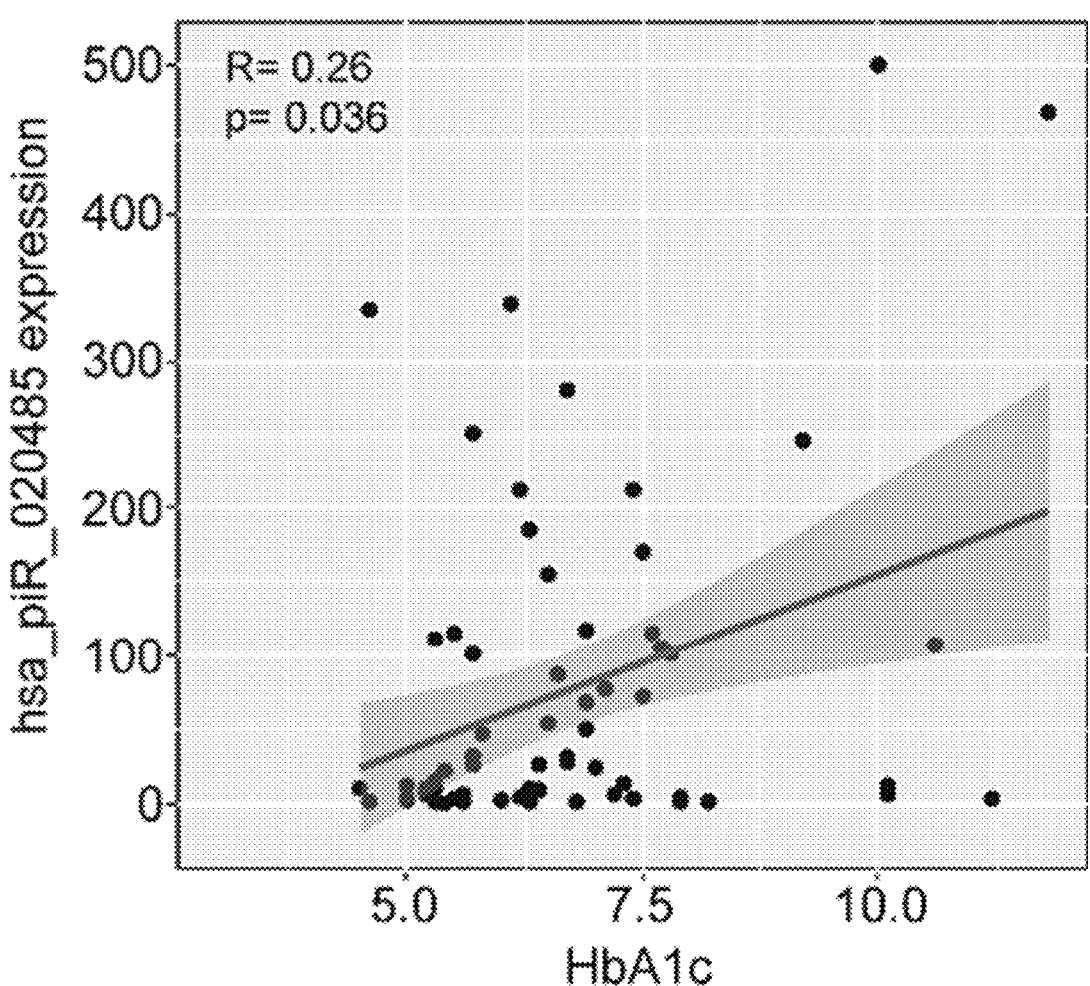
FIG. 1C depicts a scatter plot showing the correlation between hsa_piR_020485 expression and HbA1c levels, with a weak but statistically significant positive correlation ($R=0.26$, $p=0.036$).

The increase in hsa_piR_020485 expression in T2DM individuals when compared to healthy individuals is illustrated in FIG. 1A. A receiver operating characteristic analysis demonstrated that hsa_piR_020485 expression has a strong discriminative power when differentiating between healthy individuals and individuals suffering from T2DM (see FIG. 1B). The positive, statistically significant correlation between hsa_piR_020485 expression and HbA1c levels is illustrated in FIG. 1C.

It is to be understood that the Biomarker for Detecting and Treating Type II Diabetes is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

---

---

I claim:

1. A method of treating Type II Diabetes Mellitus in a subject, comprising:

obtaining a urine sample from the subject;

isolating urinary extracellular vesicles from the urine sample;

isolating total RNA from the urinary extracellular vesicles;

quantifying hsa_piR_020485 expression levels in the total RNA;

determining if the hsa_piR_020485 levels exceed a threshold; and administering at least one treatment for Type II Diabetes Mellitus to the subject;

wherein the at least one treatment comprises administering a pharmaceutical and the pharmaceutical is selected from the group consisting of metformin, a sulfonylurea, a glinide, a thiazolidinedione, a DPP-4 inhibitor, a GLP-1 receptor agonist, and a SGLT2 inhibitor.

2. The method of claim 1, wherein the quantifying comprises using next-generation sequencing.

\* \* \* \* \*

SEQUENCE LISTING

```
Sequence total quantity: 1
SEQ ID NO: 1              moltype = RNA  length = 30
FEATURE                   Location/Qualifiers
source                    1..30
                          mol_type = other RNA
                          organism = Homo sapiens
SEQUENCE: 1
ggcgggagta actatgactc tcttaaggta                                  30
```